US012649842B2

(12) United States Patent (10) Patent No.: US 12,649,842 B2
Radespiel et al. (45) Date of Patent: Jun. 9, 2026

(54) CURABLE COMPOSITION

(71) Applicant: BYK-Chemie GmbH, Wesel (DE)

(72) Inventors: Tina Radespiel, Voerde (DE); Birthe Borup, Wesel (DE); Josephine Thielmann, Surberg (DE); Christian Biecker, Hünxe (DE)

(73) Assignee: BYK-Chemie GmbH, Wesel (DE)

( * ) Notice: Subject to any disclaimer, the term of this patent is extended or adjusted under 35 U.S.C. 154(b) by 927 days.

(21) Appl. No.: 17/625,796

(22) PCT Filed: Jul. 8, 2020

(86) PCT No.: PCT/EP2020/069186
§ 371 (c)(1),
(2) Date: Jan. 10, 2022

(87) PCT Pub. No.: WO2021/005087
PCT Pub. Date: Jan. 14, 2021

(65) Prior Publication Data
US 2022/0315728 A1     Oct. 6, 2022

(30) Foreign Application Priority Data
Jul. 11, 2019    (EP) ..................................... 19185847

(51) Int. Cl.
C08K 3/011 (2018.01)
C08J 5/04 (2006.01)
C08K 3/013 (2018.01)
C08K 5/14 (2006.01)
C12N 9/08 (2006.01)

(52) U.S. Cl.
CPC ................. C08K 3/011 (2018.01); C08J 5/04 (2013.01); C08K 3/013 (2018.01); C08K 5/14 (2013.01); C12N 9/0065 (2013.01); C08J 2367/06 (2013.01); C12Y 111/01006 (2013.01); C12Y 111/01007 (2013.01)

(58) Field of Classification Search
CPC ........ C08J 2367/06; C08K 3/011; C08K 5/14; C08L 67/06; C12N 9/0065; C12Y 111/01006; C12Y 111/01007
See application file for complete search history.

(56) References Cited

U.S. PATENT DOCUMENTS

| | | | |
|---|---|---|---|
| 5,747,597 A | 5/1998 | Fujita et al. | |
| 6,306,991 B1 | 10/2001 | Fischer et al. | |
| 9,150,751 B2 | 10/2015 | Arumugam | |
| 2004/0122126 A1* | 6/2004 | Wu ........................... | C08F 4/00 |
| | | | 523/115 |
| 2014/0323613 A1 | 10/2014 | Koers et al. | |

FOREIGN PATENT DOCUMENTS

| | | | |
|---|---|---|---|
| CN | 102516570 B | | 1/2014 |
| EP | 2589629 | | 5/2013 |
| JP | 2014034551 A | * | 2/2014 |
| WO | 2004067582 A1 | | 8/2004 |
| WO | 2011138431 | | 11/2011 |
| WO | 2012085016 A1 | | 6/2012 |

OTHER PUBLICATIONS

JP-2014034551-A (Feb. 24, 2014) machine translation.*
International Search Report and Written Opinion for International Application No. PCT/EP2020/069186 dated Oct. 21, 2020 (10 pages).

* cited by examiner

*Primary Examiner* — Ana L. Woodward

(57) ABSTRACT

A composition comprising a) a curable resin or prepolymer component having ethylenically unsaturated polymerizable groups, b) an ethylenically unsaturated polymerizable monomer, c) an oxidoreductase and d) at least one of an organic peroxide and hydrogen peroxide, wherein the composition comprises between 0.0 and 20.0% by weight of water, calculated on the total weight of the composition.

16 Claims, No Drawings

CURABLE COMPOSITION

The present invention relates to a composition comprising a curable resin having ethylenically unsaturated polymerizable groups, an ethylenically unsaturated polymerizable monomer, at least one of an organic peroxide and hydrogen peroxide and an oxidoreductase, a kit of parts for preparing the composition and a process for forming a three-dimensional shaped part.

Thermoset resins such as unsaturated polyester resins, epoxyacrylate resins, urethane acrylate resins and the like including unsaturated polyesters, are commonly employed in a wide variety of products, such as casting materials and fiber reinforced materials. Unsaturated polyester resins are usually condensation products of dicarboxylic acids or anhydrides with difunctional alcohols, to provide backbone unsaturation needed for crosslinking. Polyester resins are usually diluted in a vinyl functional monomer such as styrene. The vinyl functional monomers are used to reduce the viscosity of the polyester resin and to act as a crosslinking agents. Polymerization is initiated by free radicals generated from ionizing radiation or by the photolytic or thermal decomposition of a radical initiator.

The radical initiator, usually a peroxide, decomposes into highly reactive peroxide radicals that start the radical polymerisation of the unsaturated polyesters with the vinyl functional monomers. The radical initiator is activated by accelerators, promoting the decomposition of the radical initiator, which eventually leads to the curing of the resin, generally at room temperature. Commonly used as accelerators are cobalt metal salts, like cobalt naphthenate, cobalt octoate, or cobalt neodecanoate. However, cobalt has an adverse impact on the environment, due to its hazardousness to humans, animal beings and plants. It cannot be readily degraded to reduce its detrimental influence and is labelled as carcinogenic. Therefore, there is a need for alternative accelerators used in the curing of unsaturated polyester resins. It has been found that certain enzymes can act as biobased accelerators for the crosslinking of certain kinds of polymers.

For example, U.S. Pat. No. 6,306,991 relates to a method of crosslinking polymers and more particularly to catalytic crosslinking of polymers having oxidatively crosslinkable functional groups. The oxidatively crosslinkable functional groups are crosslinked by contacting the oxidative polymer with a catalytic amount of an oxidizing enzyme. Nonetheless, the drawback of said method is that it is only applicable in aqueous coating compositions.

Accelerators are therefore required which are non-carcinogenic and biodegradable and may be employed in non-aqueous thermosetting resins. The present invention addresses these needs. It has been surprisingly found that a composition comprising a) a curable resin or prepolymer component having ethylenically unsaturated polymerizable groups, b) an ethylenically unsaturated polymerizable monomer, c) an oxidoreductase and, d) at least one of an organic peroxide and hydrogen peroxide, wherein the composition comprises between 0.0 and 20.0% by weight of water, calculated on the total weight of the composition overcomes the drawbacks of the state of the art mentioned above.

The composition comprises a curable resin or prepolymer component having ethylenically unsaturated polymerizable groups a) and an ethylenically unsaturated polymerizable monomer b).

The term prepolymer refers to a monomer or system of monomers that have been reacted to an intermediate molecular mass state. This material is capable of further polymerization by reactive groups to a fully cured high molecular weight state. As such, mixtures of reactive polymers with un-reacted monomers may also be referred to as prepolymers.

Curing is a chemical process that produces the toughening or hardening of a polymer material by cross-linking of polymer chains. The curing process can be conducted by any method known in the art. Curing can be performed at room temperature or at elevated temperatures. It is possible to start at ambient temperature and then use the exothermal behavior of the system to achieve the temperature increase. It is also possible to force temperature increase by external heating, optionally in combination with pressure.

Suitable curable resins are thermosetting resins, for example unsaturated polyester resins, epoxy(meth)acrylate resins, urethane (meth)acrylate resin, unsaturated polyester (meth)acrylate and the like. Epoxy(meth)acrylate resins are often referred to as "vinyl ester resins".

Typically, these unsaturated polyesters are the product of unsaturated mono- or dibasic acids with difunctional alcohols used in the manufacture of the aforementioned unsaturated polyester. Suitable examples of $\alpha,\beta$-unsaturated dibasic acids are maleic acid, maleic anhydride, fumaric acid, itaconic acid and itaconic anhydride.

Suitable dibasic acids are phthalic acid, phthalic anhydride, halogenated phthalic anhydride, isophthalic acid, terephthalic acid, tetrahydrophthalic acid, tetrahydrophthalic anhydride, hexahydrophthalic acid, hexahydrophthalic anhydride, hexahydroterephthalic acid, hexahydroisophthalic acid, succinic acid, malonic acid, glutaric acid, adipic acid, sebacic acid, 1,12-dodecane dicarboxylic acid, 2,6-naphthalene dicarboxylic acid, 2,7-naphthalene dicarboxylic acid, 2,3-naphthalene dicarboxylic acid, 2,3-naphthalene dicarboxylic acid anhydride, 4,4'-biphenyldicarboxylic acid, as well as dialkylesters of the aforementioned, and the like.

Suitable monobasic acids include benzoic acid, stearic acid, oleic acid, linolenic acid, linoleic acid, palmitic acid and the like, including combinations thereof.

Examples for suitable multifunctional alcohols are polyhydric alcohols which include, for example, ethylene glycol, diethylene glycol, triethylene glycol, polyethylene glycol, propylene glycol, dipropylene glycol, polypropylene glycol, 2-methyl-1,3-propane diol, 1,3-butane diol, neopentylglycol, bisphenol A hydroxide, 1,4-butane diol, adduct of bisphenol A and propylene oxide or ethylene oxide, 1,2,3, 4-tetrahydroxybutane, glycerin, trimethylol propane, 1,3-propane diol, 1,2-cyclohexane glycol, 1,3-cyclohexane glycol, 1,4-cyclohexane glycol, 1,4-cyclohexane dimethanol, paraxylene glycol, dicyclohexyl-4,4'-diol, 2,6-decalin glycol, 2,7-decalin glycol, and mixtures thereof. Monohydric alcohols include benzyl alcohol, hydroxy(dicyclopentadiene), cyclohexyl alcohol, 2-ethylhexyl alcohol, lauryl alcohol, stearyl alcohol, and mixtures thereof.

The urethane (meth)acrylate component is a product of a difunctional or polyfunctional isocyanate with a hydroxyl-functionalized (meth)acrylate. The preparation of urethane (meth)acrylates is well known to those skilled in the art. Suitable isocyantes may include 2,4-toluene diisocyanate, 2,6-toluene diisocyanate (TDI), 4,4'-diphenylmethane diisocyanate (MDI), 1,5-naphthalene diisocyanate (NDI), tetramethylxylene diisocyanate (TMXDI), hexamethylene diisocyanate (HDI), 4,4'-dicylohexylmethane diisocyanate ($H_{12}$MDI), 4,6'-xylene diisocyanate (XDI), isophorone isocyanate (IPDI), 2,2,4-trimethyl-1,6-hexamethylene diisocyanate (TMDI), paraphylene diisocyanate (PPDI), cyclo-hexyldiisocyanate (CHDI), 3,3'-tolidene 4,4'-diisocyanate (TODI) and 3,3'-dimethyl-diphenylmethane 4,4'-diisocya-nate (DDI), including their polymeric forms.

Hydroxy-functionalized (meth)acrylates that may be used in the preparation of the urethane (meth)acrylate monomer component include hydroxyethyl methacrylate (HEM A), hydroxypropyl methacrylate (HPMA), hydroxyethyl acry-late (HEA), hydroxypropyl acrylate (HP A) and related compounds.

The epoxy(meth)acrylate may be a di(meth)acrylate of, for example, a bisphenol-type epoxy resin, novolak-type epoxy resin, 1,6-naphthalene-type epoxy resin or the like, which is obtained by means of reacting any of the afore-mentioned epoxy resin (alone or in combination), and a unsaturated monobasic acid under the presence of an esteri-fication catalyst.

Concerning the ethylenically unsaturated polymerizable monomer b), it is possible to use any ethylenically unsatu-rated monomer and ethylenically unsaturated oligomer con-ventionally used in unsaturated polyester resins, which can crosslink with an unsaturated polyester. The ethylenically unsaturated polymerizacle monomer is preferably a mono-mer containing a vinyl group. Preferably, one of a (meth) acrylate group, styryl group, allyl group and vinylether group.

Examples of the aforementioned vinyl monomer include alpha-methylstyrene, chlorostyrene, dichlorostyrene, divi-nylbenzene, t-butylstyrene, vinyltoluene, vinyl acetate, dial-lylphthalate, triallylcyanurate, acrylic esters, (meth)acrylic esters, methyl (meth) acrylate, ethyl (meth)acrylate, n-butyl (meth)acrylate, i-butyl (meth) acrylate, t-butyl (meth)acry-late, 2-ethylhexyl (meth) acrylate, lauryl (meth)acrylate, cyclohexyl (meth)acrylate, benzyl (meth) acrylate, stearyl (meth)acrylate, tridecyl (meth)acrylate, dicyclopenteny-loxyethyl (meth) acrylate, ethylene glycol monomethylether (meth)acrylate, ethylene glycol monoethylether (meth)acry-late, ethylene glycol monobutylether (meth) acrylate, ethyl-ene glycol monohexylether (meth)acrylate, ethylene glycol mono-2-ethylhexylether (meth)acrylate, propylene glycol monomethylether (meth)acrylate, propylene glycol mono-ethylether, propylene glycol monobutylether (meth)acrylate, (meth) acrylate, propylene glycol monohexylether (meth) acrylate, propylene glycol mono-2-ethylhexylether (meth) acrylate, ethylene glycol di(meth) acrylate, diethylene gly-col di(meth)acrylate, triethylene glycol di(meth) acrylate, neopentyl glycol di(meth)acrylate, trimethylolpropane tri (meth) acrylate, pentaerythritol tetra(meth)acrylate, dipen-taerythritol penta(meth) acrylate, dipentaerythritol hexa(m-eth)acrylate, N-vinylpyrolidone and the like. These aforementioned monomers may be used alone or in combi-nation.

The enzyme used in the composition is an oxidoreductase c). Oxidoreductases are classified as EC 1. The Enzyme Commission number (EC number) is a numerical classifi-cation scheme for enzymes, based on the chemical reactions they catalyze published by the Nomenclature Committee of the International Union of Biochemistry and Molecular Biology. Every enzyme code consists of the letters "EC" followed by certain numbers separated by periods. Those numbers represent a progressively finer classification of the enzyme.

The at least one oxidoreductase is preferably a peroxidase (EC 1.11.1), which are enzymes defined as oxidoreductases acting on peroxide as electron acceptor.

More preferably, the enzyme is one or more of a laccase, polyphenol peroxidase, horseradish peroxidase, soybean peroxidase, pea peroxidase, guar beans peroxidase, gar-banzo beans peroxidase, runner beans peroxidase, rice per-oxidase, cotton peroxidase and mixtures thereof. Even more preferably, the enzyme is a peroxidase (EC 1.11.1.7), cata-lase (EC 1.11.1.6) or mixtures thereof. Most preferably, the enzyme is a horseradish peroxidase.

It is preferred, that amounts of the enzyme in the range of 0.01 to 40.00 mg/g are employed; more preferably 0.01 to 30.00 mg/g and most preferably 0.01 to 25.00 mg/g based on the weight of components a)+b). In a preferred embodiment, 0.10 to 30.00 mg/g enzyme are employed. In another pre-ferred embodiment, 0.50 to 30.00 mg/g enzyme are employed. In a different preferred embodiment, 0.30 to 40.00 mg/g enzyme are employed, more preferred 0.30 to 30.00 mg/g and most preferred 0.30 to 25.00 mg/g enzyme, all calculated on the weight of components a)+b).

The enzymes utilized according to the invention can generally be of any origin. The oxidoreductase may suitably be from plant, fungal, mammalian, yeast or bacterial origin. Horseradish peroxidase for example is a glycoprotein with a molecular weight of about 40,000, and may suitably extracted from the horseradish root, which is a perennial plant of the family Brassicaceae. Catalase, with a molecular weight of about 240 kDa may preferably be extracted from bovine liver.

Examples of suitable fungi are *Collybia, Coprinus, For-nus, Lentinus, Pleurotus, Aspergillus, Neurospora, Podospora, Phlebia*, in particular *P. radiata, Coriolus*, in particular *C. hirsitus, Botrytis, Polyporus*, in particular *P. pinsitus* and *P. versicolor, Rhizoctonia solani, Scytalidium*, in particular *S. thermophilium, Pyricularia*, in particular *P. oryzae, Coprinus*, in particular *C. cinereus, Trametes*, in particular *T. hirsuta, T. villosa* and *T. versicolor, Coriolopsis gallica, Phanerochaete chrysosporium, Heterobasidion annosum, Spiniger meineckellus* and *Myceliophthora ther-mophila*.

The oxidoreductase may preferably be derived from a bacterium that is selected from the group comprised of *Bacillus, Pseudomonas, Streptomyces, Corynebacterium, Micrococcus* and *Azospirillum*.

The oxidoreductase can be either directly isolated from the corresponding source or be produced by means of a recombinant technology. The oxidoreductase is suitably an extract from a natural source or produced via homologous or heterologous expression.

Heterologous expression denotes for the expression of a gene in a system that naturally do not contain the gene, e.g. certain type of bacteria. The recombinant production takes place in a different host cell thereby that the enzyme encoding DNA section is isolated from the source of origin and introduced into a host cell. Homologous expression on the other hand refers to over-expression of a gene in a system where the gene naturally exists. In both cases, the expression and over-expression of the specific gene leads to the pro-duction of the designated enzyme eventually. On the con-trary, natural source denotes for the source of the enzyme, where the designated enzyme is synthesized without manipulating the gene expression by processes other than breeding and crossing. For example, the oxidoreductase may suitably be extracted from the horseradish root as natural source. Appropriate methods are sufficiently familiar to the person skilled in the art.

The composition further comprises at least one of an organic peroxide and hydrogen peroxide d). Suitable examples for organic peroxides are benzoyl peroxide, t-butyl hydroperoxide, diacylperoxides, hydroperoxides, ketone peroxides, peroxyesters, peroxyketals, dialkyl peroxides, alkyl peresters and percarbonates, methyl ethyl ketone peroxide, benzoyl peroxide, acetyl acetone peroxide and cumene hydroperoxide. Combinations of two or more peroxides may be also used to cure the resin.

Generally, the at least one of an organic peroxide and hydrogen peroxide is employed in an amount from 0.05 to 10.00% by weight, preferably 0.10 to 7.00% by weight and more preferably 0.10 to 4.00% by weight based on the total weight of the total composition.

The composition comprises 0.0 to 20.0% by weight of water. Suitably, the composition comprises 0.0 to 15.0% of water, more suitably 0.0 to 10.0% by weight of water. Most suitably, the composition comprises 0.0 to 5.0% by weight of water, calculated on the total weight of the composition.

Preferably, the composition further comprises a mediator for enzymatic initiation of radical polymerization. Examples for such mediators are 4-hydroxybenzoic acid, 4-hydroxy-acetophenone, pentane-2,4-dione, nitroso compounds and hydroxyamine compounds, such as cycloaliphatic NO or NOH containing compounds, heterocyclic NO or NOH containing compounds, aromatic NO or NOH containing compounds, phenolic compounds with at least one, preferably two or more, phenolic hydroxyl group or groups, phenothiazine, phenyl compounds, heterocyclic compounds, polyoxometalates, 2,4-pentanedione and derivatives of these compounds, as well as 6-Hydroxy-2-naphthoic acid, 7-Methoxy-2-naphthol, 4-Hydroxycoumarin, n-Hydroxyph-thalimide, Tetronic acid, 1,3-Cyclopentanedione, 10-Meth-ylphenothiazine, Phenylacetic acid, 4-Hydroxybenzonitrile, 4-Hydroxybenzyl alcohol, 4-Hydroxybenzaldehyde, 4-Hy-droxybenzoic acid, 4"-Hydroxyacetanilide, 4"-Hydroxyac-etophenone, 4"-hydroxy-4-biphenylcarboxylic acid, 4"-hy-droxy-4-biphenylcarboxylic acid, Vanillin, Dibenzoylmethane, Benzoylacetone and mixtures thereof. It is preferred that the mediator is at least one of 6-hydroxy-2-naphtoic acid or Acetylacetone (ACAC).

The mediator is preferably present in an amount of 0.01 to 5.00 mmol/g, more preferably 0.02 to 3.00 mmol/g and most preferably 0.02 to 2.00 mmol/g, based on the weight of components a)+b).

Suitably, the composition is liquid at a temperature of 23° C.

The composition generally comprises between 0.0 and 40.0% of organic solvent. An example of a suitable organic solvent is dimethyl sulfoxide. Preferably, the organic solvent is present in an amount of 0.5 to 30.0% by weight, more preferably in an amount of 1.0 to 20.0% by weight and most preferably 1.0 to 10.0% by weight, calculated on the total weight of the composition.

Moreover, the composition suitably comprises solid particles selected from fillers, pigments, fibers, and combinations thereof. Fillers may be used at levels up to about 60% by weight, based on the total weight of the composition and may include calcium carbonate, calcium sulfate, aluminum, aluminium trihydrate, aluminium hydroxide, hydraulic silicates, clay, talc, barium sulfate, silica powder, glass powder, glass beads, microcellulose, silica sand, river sand, marble waste, crushed stone or any combinations thereof.

Fiber reinforced composite materials comprise fibers embedded in a polymer matrix. The polymer matrix serves as binder between the fibers. The fibers generally improve the mechanical properties of composite material, as compared to the matrix polymer alone. The fibers may be inorganic or organic. Suitable fibers are glass fiber, carbon fiber, basalt fiber and polymeric fibers. They may generally be employed up to 60% by weight, based on the total weight of the composition.

Carbon fibers include amorphous carbon fibers and graphite fibers. Carbon fibers produced from various starting materials are equally suitable, for example, carbon fibers prepared from polyacrylonitrile, pitch, or rayon. The carbon fibers may have undergone a chemical or mechanical surface pretreatment, for example with known sizing agents during fiber manufacture. Carbon fibers, which have not been subjected to specific pretreatments, may likewise be employed. Depending on the intended end use, the carbon fibers may be present as filament fibers, as staple fibers, or as chopped fibers. In some embodiments, the carbon fibers are present as a woven or non-woven fabric. On other embodiments, the carbon fibers are present as a roving.

All known kinds of pigments may be used in the composition according to the invention. Inorganic or organic pigments and mixtures thereof may suitably be employed. Typically, the organic pigments are color pigments. This refers to colored material made of organic compounds with pigment properties. In some embodiments, the inorganic and organic pigments may preferably be used up to 60% by weight, based on the total weight of the composition.

In one embodiment, the composition comprises
  a) 30.00 to 90.00% by weight of a curable resin or prepolymer component having ethylenically unsaturated polymerizable groups,
  b) 10.00 to 70.00% by weight of an ethylenically unsaturated polymerizable monomer,
  c) 0.01 to 40.00 mg/g of an oxidoreductase and
  d) 0.05 to 10.00% by weight of an at least one of an organic peroxide and hydrogen peroxide
  wherein the composition comprises between 0.00 and 20.00% by weight of water, calculated on the total weight of the composition.

Curing of a thermosetting resin will initiate when at least all four components, i.e. the curable resin or prepolymer, the ethylenically unsaturated polymerizable monomer, the oxidoreductase and the peroxide, are mixed together. Therefore, to ensure a storage-stable composition, which can be prepared shortly before the application the invention further relates to a kit of parts for preparing the composition according to the invention, comprising
  I. a binder module comprising
    a) a curable resin or prepolymer component having ethylenically unsaturated polymerizable groups,
    b) an ethylenically unsaturated polymerizable monomer, and
    c) an oxidoreductase, and
  II. a hardener module comprising at least one of an organic peroxide and hydrogen peroxide,
    wherein each module comprises between 0.0 and 20.0% by weight of water, calculated on the weight of the respective module.

Additionally, the thermosetting resin can be prepared by mixing three different modules, to achieve the desired curing. Therefore, the invention also relates to a kit of parts for preparing the composition according to the invention, comprising
  I. a binder module comprising
    a) a curable resin or prepolymer component having ethylenically unsaturated polymerizable groups,
    b) an ethylenically unsaturated polymerizable monomer,
  II. a hardener module comprising at least one of an organic peroxide and hydrogen peroxide, and
  III. an activator module comprising an oxidoreductase, wherein the binder module and the hardener module comprise between 0.0 and 20.0% by weight of water, calculated on the weight of the respective module.

The invention also deals with a process of forming a three-dimensional shaped part comprising the steps of i. preparing a composition according to the invention, ii. bringing the composition in a desired three-dimensional shape, and iii. curing the composition by radical polymerization.

Examples for three-dimensional shaped parts are components or parts of boats, tanks (e.g. for oil, water, chemical products), pipes and tubes (e.g. for drinking and waste water), wall covering and sheathing, caravans, bathroom and lavatory interior (e.g. sinks, bathtubs, shower trays), seats (e.g. for busses, trains, stadiums), parts for automotives like cars, trucks, tractors (e.g. radiator cowls, trunk lids, air deflectors, spoilers, attachment parts, roofs), doors, window and casement frames, profiles, battery housings, parts for wind power plants like blades, housings, and the like.

Step ii) of the process of forming a three-dimensional shaped part is preferably carried out by introducing the composition according to the invention in a mold.

The process of forming a three-dimensional shaped part may suitably include the step of impregnating fibers with the composition according to the invention. Examples for preferred fibers are mentioned above.

Typical procedures comprise sheet molding compounding (SMC), bulk molding compounding (BMC), infusion molding (RIM—resin infusion molding, RTM—resin transfer molding), compression molding, VARI (vacuum applied resin infusion), filament winding, pultrusion, and autoclave curing.

Further components may be present in the composition, in particular such components which are typically used in manufacturing thermosetting resins. Examples of such components include thickeners, UV stabilizers, mold release agents, wetting and dispersing additives, rheology additives, surface additives and anti-foaming agents.

EXAMPLES

Description of Raw Materials Used

TABLE 1

| Raw materials | | |
| --- | --- | --- |
| Trade designation | Chemical description | Supplier |
| Palatal P4-01 | UP resin based on orthophthalic acid and standard glycols dissolved in >25-<50% styrene | AOC Aliancys |
| Derakane Momentum 411-350 | Epoxy vinyl ester resin based on bisphenol-A epoxy resin dissolved in >40-<50% styrene | Ashland |
| Palatal A-410 | UP resin based on isophthalic acid and neopentylglycol dissolved in >25-<50% styrene | AOC Aliancys |
| Palatal A 400-01 FC | UP resin based on isophthalic acid and standard glycols dissolved in >25-<50% styrene | AOC Aliancys |
| Advalite VH-1223 | Vinyl hybrid resin, styrene free | Reichhold |
| Advalite Vinyl hybrid 35060-00 | Vinyl hybrid resin | Reichhold |
| Atlac Premium 100 | Vinyl ester resin dissolved in methacrylate, styrene free | AOC Aliancys |
| Butanox M-50 | Methyl ethyl ketone peroxide dissolved in dimethylphthalate | Akzo Nobel |
| Trigonox 44B | Acetylacetone peroxide dissolved in | Akzo Nobel |

TABLE 1-continued

| Raw materials | | |
| --- | --- | --- |
| Trade designation | Chemical description | Supplier |
| | solvent mixture | |
| Butanox LPT-IN | Methyl ethyl ketone peroxide dissolved in diisononylphthalate | Akzo Nobel |
| Butanox M-50VR | Methyl ethyl ketone peroxide dissolved in dimethylphthalate with dye | Akzo Nobel |
| | Hydrogen peroxide, 30% | Merck |
| | Dimethyl sulfoxide, Ph. Eur. | VWR |
| | Water, ultrapure | |
| Rhodiasolve PolarClean HSP | Pentanoic acid, 5-(dimethylamino)-2-methyl-5-oxo-methyl ester | Solvay |
| Tamisolve NxG | 1-Butylpyrrolidin-2-one | Eastman |
| | 2-Pyrrolidone | |
| | n-Formylmorpholine | |
| | n-Methyl-2-pyrrolidone | |
| | Peroxidase | various supplier |
| | Catalase | various supplier |
| | Acetylacetone (ACAC) | Sigma Aldrich |
| | 6-Hydroxy-2-naphtoic acid | AlfaAesar |
| NL-49P | Cobalt(ll) 2-ethylhexanoate, 1% Co | Akzo Nobel |

Sample Preparation 10 g resin (Palatal P4-01 if not mentioned otherwise) were placed in a 50 ml PE-plastic beaker. Mediators in solid form (like 6-Hydroxy-2-naphtoic acid) were dissolved in DMSO or water. Liquid mediators (like ACAC) were added directly to resin. The solid enzyme was placed in a 50 ml centrifugation tube or 5 ml reaction tube, depending on needed final amount, and was dissolved in mediator-DMSO-solution, water, or pure DMSO. Liquid enzyme was added directly to the resin. The enzyme solution was vortexed and shortly centrifuged at 4° C. and 6000 rcf. All components were added to the resin as follows: first the enzyme-(mediator)-solution and the peroxide at the end. In case of the mediator being liquid, the enzyme-solution was added first and the mediator was added afterwards, followed by addition of the peroxide. After each addition, the mixture was stirred with a spatula by hand. All w % are calculated on the weight of the resin (component a+b).

Shore Hardness Measurement

After addition of all components, plastic beakers were closed with a cap. Incubation was performed in a Thermomixer comfort (Eppendorf) for 2, 24, 48 hours at 24° C. with closed lid. Shore A hardness measurements of samples were made with digitest II Type DTAA (Bareiss) after 2, 24 and 48 hours according to DIN ISO 7619.

Determination of Gel-Time

After addition of all components, samples were directly filled in test tubes (Duran #261302106) up to the mark (4 cm), corresponding to about 5 g of sample. Measurement was started immediately and gel-time was measured up to 2 hours at 23° C. with Gelnorm-Geltimer (Gel Instrumente AG) with measurement pin (H.Saur #020.30).

Non-Inventive Control with Accelerator NL-49P and Addition of Water

The samples were prepared as described above (see sample preparation) using the amounts as described in table 2 followed by incubation in a Thermomixer comfort (Eppendorf) for 2, 24, 48 hours at 24° C. with closed lid.

TABLE 2

| | |
|---|---|
| water: | 0-10.0 wt % |
| accelerator (NL-49P): | 1 wt % |
| peroxide (Butanox M-50): | 2 wt % |

TABLE 3

| Results | |
|---|---|
| water [wt %] | started to cure [h] |
| 0 | <0.15 |
| 4.3 | 15 |
| 6.0 | 15 |
| 8.0 | 24 |
| 10.0 | 24 |

Started to cure was determined by poking the reaction mixture with a spatula. When poking with a spatula left an indentation in the reaction mixture, and no flow-back of the reaction mixture to the indentation was observed, gelation was considered to have occurred.

The table shows that an increased addition of water resulted in an increased reaction time of curing with the Cobalt accelerator.

Variation of Enzyme Concentration

The samples were prepared as described above (see sample preparation) using the amounts as described in table 4 followed by incubation in a Thermomixer comfort (Eppendorf) for 2, 24, 48 hours at 24° C. with closed lid. The enzyme (peroxidase, Sigma Aldrich, #P8250) was dissolved in 4.3 wt % water.

TABLE 4

| | |
|---|---|
| enzyme peroxidase, solid: | 0-17 mg/g resin |
| water: | 4.3 wt % |
| mediator (ACAC): | 0.12 mmol/g resin |
| peroxide (Butanox M50): | 2 wt % |

TABLE 5

| Results | | |
|---|---|---|
| enzyme | started to cure [h] | |
| [mg solid/g resin] | with mediator | without mediator |
| 0.0 | x | x |
| 0.4 | x | 167 |
| 2.0 | 65 | 65 |
| 3.0 | 49 | 49 |
| 4.0 | 42 | 42 |
| 7.0 | 24 | 49 |
| 9.0 | 18 | 17 |
| 13.0 | 15 | 15 |
| 17.0 | 7 | 15 | x: "no curing"

The curing was observed visually and determined as described above.

The results show that with an increasing amount of enzyme the reaction time decreased. By addition of the mediator, the reaction time decreased further.

Variation of Water Concentration

The samples were prepared as described above (see sample preparation) using the amounts as described in table 6 followed by incubation in a Thermomixer comfort (Eppendorf) for 2, 24, 48 hours at 24° C. with closed lid. The enzyme (peroxidase, Sigma Aldrich, #P8250) was dissolved in various water concentrations.

TABLE 6

| | |
|---|---|
| enzyme peroxidase, solid: | 17 mg/g resin |
| water: | 4-10 wt % |
| mediator (ACAC): | 1.2 mmol/g resin |
| peroxide (Butanox M-50): | 2 wt % |

TABLE 7

| Results | | |
|---|---|---|
| | started to cure [min] | |
| water [wt %] | with mediator | without mediator |
| 4 | 1440 | 1440 |
| 6 | 60 | 180 |
| 8 | 60 | 60 |
| 10 | 60 | 60 |

Curing was observed visually and determined as described above.

With increasing water content, the reaction time decreased. With addition of mediator, the reaction time decreased even further.

Variation of Peroxide Concentration

The samples were prepared as described above (see sample preparation) using the amounts as described in table 8 followed by incubation in a Thermomixer comfort (Eppendorf) for 2, 24, 48 hours at 24° C. with closed lid. The enzyme (peroxidase, Sigma Aldrich, #P8250) was dissolved in 10 wt % water.

TABLE 8

| | |
|---|---|
| enzyme peroxidase, solid: | 17 mg/g resin |
| water: | 10 wt % |
| mediator (ACAC): | 1.2 mmol/g resin |
| peroxide (Butanox M-50): | 0.2-6.0 wt % |

TABLE 9

| Results | | |
|---|---|---|
| | started to cure [min] | |
| peroxide [wt %] | with mediator | without mediator |
| 0.2 | 60 | 120 |
| 1.0 | 36 | 36 |
| 2.0 | 36 | 500 |
| 4.0 | 300 | 1440 |
| 6.0 | 180 | 480 |

Curing was observed visually and determined as described above.

In general, lower peroxide concentrations showed shorter reaction times. The best result was achieved between 0.2 and 1.0 wt % peroxide.

Variation of Mediator Concentration

The samples were prepared as described above (see sample preparation) using the amounts as described in table 10 followed by incubation in a Thermomixer comfort (Eppendorf) for 2, 24, 48 hours at 24° C. with closed lid. The enzyme (peroxidase, Sigma Aldrich, #P8250) was dissolved in 10 wt % water.

TABLE 10

| enzyme peroxidase, solid: | 17 mg/g resin |
|---|---|
| water: | 10 wt % |
| mediator (ACAC): | 0.00-0.24 mmol/g resin |
| peroxide (Butanox M-50): | 1 wt % |

TABLE 11

| | | Results | | |
|---|---|---|---|---|
| mediator [mmol/g resin] | started to cure [min] | visual evaluation | | |
| | | after 2 h | after 24 h | after 48 h |
| 0.00 | 0-36 | 3.0 | 2.0 | 1.7 |
| 0.01 | 0-36 | 3.3 | 1.7 | 1.3 |
| 0.06 | 0-36 | 2.3 | 1.3 | 1.3 |
| 0.12 | 0-36 | 2.7 | 1.7 | 1.3 |
| 0.24 | 0-36 | 3.0 | 2.0 | 1.7 |

1 = very good; 2 = good; 3 = satisfactory

Curing was observed visually and determined as described above.

Moreover, the hardness, thickness and homogeneity of the resin were assessed. The parameters were evaluated visually and additionally by poking the resin with a spatula. Subsequently, the criteria summarized in the table above were applied. 3 denotes for medium thick sample, which is soft to solid with residual liquid; 2 denotes for a thick sample, solid and with a lower content of residual liquid and 1 denotes for a thick sample, which is very solid with almost no residual liquid.

The best results were achieved between 0.01 and 0.06 mmol ACAC/g resin.

Increase of Water Concentration

The samples were prepared as described above (see sample preparation) using the amounts as described in table 12. The enzyme (peroxidase, Sigma Aldrich, #P8250) was dissolved in water concentrations between 10 and 20 w %.

TABLE 12

| enzyme peroxidase, solid: | 17 mg/g resin |
|---|---|
| water: | 10-20 wt % |
| mediator (ACAC): | 0.05 mmol/g resin |
| peroxide (Butanox M-50): | 0.5 wt % |

TABLE 13

| | | Results | |
|---|---|---|---|
| water [wt %] | gel-time [min] | Shore A after 24 h | Shore A after 48 h |
| 10 | 22 | 71 | 80 |
| 15 | 0 | 66 | 76 |
| 20 | 50 | 47 | 78 |

The best result was reached with 10 wt % water content. With higher water concentrations, the gel-time increased and but the Shore A hardness of the final sample decreased.

Peroxidases from Various Suppliers

The samples were prepared as described above (see sample preparation) using the amounts as described in table 14. The enzymes were dissolved in 10 wt % water.

TABLE 14

| enzyme peroxidase, solid: | 17 mg/g resin |
|---|---|
| water: | 10 wt % |
| mediator (ACAC): | 0.5 mmol/g resin |
| peroxide (Butanox M-50): | 0.5 wt % |

The activity of the enzyme was determined by using ABTS as substrate. 1 U stands for one unit which oxidizes 1.0 μmole of 2,2″-azino-bis (3-ethylbenzthiazoline-6-sulfonic acid) per minute at pH 5.0 at 25° C., measured at A=405 nm (Spark, Tecan).

TABLE 15

| | | Results | | | |
|---|---|---|---|---|---|
| supplier | article number | enzyme activity [U/mg protein] | gel-time [min] | Shore A after 24 h | Shore A after 48 h |
| abcr | AB348238 | 313 | 41 | 44 | 77 |
| Alfa Aesar | J60026 | 109 | 58 | 41 | 76 |
| Amano | Amano PO-3 | 652 | 11 | 83 | 85 |
| Amresco | 417 | n/a | 20 | 73 | 76 |
| BBI Solutions | 161451BBI | 497 | 25 | 79 | 85 |
| | 161453BBI | 443 | 81 | 48 | 77 |
| | 161455BBI | 412 | 133 | 52 | 87 |
| | 161457BBI | 256 | 32 | 44 | 66 |
| Biosynth | P-2000 | 236 | 92 | 33 | 71 |
| Calzyme | 100A0400 | 577 | 29 | 89 | 81 |
| | 100A0600 | 519 | 16 | 81 | 89 |
| Chemical Point | CP9003-99-0-BULK | 291 | 15 | 42 | 76 |
| Creative Enzymes | PHAM-231 | 177 | 24 | 69 | 83 |
| Faizyme | 16001 | 356 | 16 | 73 | 82 |
| | 16002 | 348 | 19 | 68 | 77 |
| | 16004 | 196 | n/a | 20 | 56 |
| | 16005 | 169 | n/a | 20 | 58 |
| Iris Biotech | LS-1217 | 266 | 37 | 43 | 76 |
| Proactive Molecular Research | P113-0165 | 260 | 16 | 59 | 69 |
| Sigma Aldrich | P8125 | 175 | 51 | 40 | 70 |
| | P8250 | 325 | 18 | 80 | 91 |
| | P8375 | 427 | 14 | 77 | 84 |
| TCI Chemicals | P0073 | 318 | 17 | 73 | 80 |

From the table it is visible, that all peroxidases showed a curing effect, irrespective of their origin from different commercial suppliers.

DMSO as Solvent

The samples were prepared as described above (see sample preparation) using the amounts as described in table 16. The enzyme (peroxidase, Sigma Aldrich, #P8250) was dissolved in various concentrations of water-DMSO mixtures. No mediator was used in this experiment.

TABLE 16

| enzyme peroxidase, solid: | 17 mg/g resin |
|---|---|
| peroxide (Butanox M-50): | 0.2 wt % |

TABLE 17

| | | | Results | |
|---|---|---|---|---|
| water [wt %] | DMSO [wt %] | gel-time [min] | Shore A after 24 h | Shore A after 48 h |
| 0 | 10 | 49 | 79 | 82 |
| 9 | 1 | 86 | 78 | 84 |
| 5 | 5 | 58 | 79 | 83 |

Without enzyme, no curing was detectable.

From the table it is visible that curing of the resin with peroxidase was also possible without any water and mediator in the system.

Curing with Various Resins and Peroxides

Experiments with Cobalt accelerator NL-49P (without enzyme) were performed as non-inventive control. The samples were prepared as described above (see sample preparation) using the amounts as described in table 18.

TABLE 18

| resin | peroxide | peroxide [wt %] | NL-49P [wt %] | gel-time [min] | Shore A after 24 h | Shore A after 48 h |
|---|---|---|---|---|---|---|
| Palatal P 4-01 | Butanox M-50 | 2 | 1.0 | 7 | 88 | 96 |
| Palatal P 4-01 | Trigonox 44B | 1 | 0.5 | 16 | 90 | 93 |
| Palatal A-410 | Trigonox 44B | 1 | 0.5 | 10 | 90 | 94 |
| Palatal A 400-01 FC | Butanox M-50 | 1 | 1.0 | 7 | 91 | 95 |
| Atlac Premium 100 | Butanox LPT-IN | 2 | 2.0 | 13 | 85 | 91 |

Experiments with Different Resins

The enzyme (peroxidase, BBI Solutions, #161451BBI) was dissolved in 10 wt % water.

TABLE 19

| | |
|---|---|
| enzyme peroxidase, solid: | 17 mg/g resin |
| mediator (ACAC): | 0.05 mmol/g resin |
| Peroxide (Butanox M-50): | 0.5 wt % |

TABLE 20

| | Results | | |
|---|---|---|---|
| resin | gel-time [min] | Shore A after 24 h | Shore A after 48 h |
| Palatal P 4-01 | 19 | 70 | 82 |
| Palatal A-410 | 10 | 75 | 89 |
| Palatal A 400-01 FC | 7 | 87 | 89 |
| Derakane Momentum 411-350 | 18 | 85 | 94 |
| Advalite VH-1223 | 39 | 29 | 33 |
| Advalite ™ Vinyl hybrid 35060-00 | n/a | 24 | 37 |
| Atlac Premium 100 | n/a | 65 | 77 |

With peroxidase, different resin systems based on unsaturated polyester, vinylester, or with acrylates or styrene as monomer could be cured.

For testing of different peroxides, Palatal P 4-01 as resin was used.

TABLE 21

| | | | | Results |
|---|---|---|---|---|
| resin | peroxide | gel-time [min] | Shore A after 24 h | Shore A after 48 h |
| Palatal P 4-01 | Butanox LPT-IN | 31 | 88 | 87 |
| Palatal P 4-01 | Butanox M-50VR | 25 | 64 | 79 |
| Palatal P 4-01 | Butanox M-50 | 19 | 70 | 82 |

With peroxidase, different peroxides could be used for curing of the resin system.

Variation of DMSO Concentration

The samples were prepared as described above (see sample preparation) using the amounts as described in table 22. The enzyme (peroxidase, Faizyme, #16001) was dis-solved in various DMSO concentrations. 6-hydroxy-2-naph-toic acid was used as mediator.

TABLE 22

| | |
|---|---|
| enzyme peroxidase, solid: | 17 mg/g resin |
| DMSO: | 2.5-20 wt % |
| mediator (6-hydroxy-2-naphtoic acid): | 0.05 mmol/g resin |
| peroxide (Butanox M-50): | 0.5 wt % |

TABLE 23

| | | Results | | |
|---|---|---|---|---|
| DMSO [wt %] | gel-time [min] | Shore A after 2 h | Shore A after 24 h | Shore A after 48 h |
| 2.5 | 36 | 20 | 83 | 87 |
| 5.0 | 4 | 85 | 97 | 98 |
| 7.5 | 5 | 90 | 97 | 97 |
| 10.0 | 5 | 89 | 97 | 97 |
| 15.0 | 4 | 73 | 94 | 95 |
| 20.0 | 6 | 66 | 90 | 90 |

The best result was reached with 7.5 wt % DMSO.

Variation of Enzyme Concentration with DMSO as Solvent

The samples were prepared as described above (see sample preparation) using the amounts as described in table 24. The enzyme (peroxidase, Faizyme, #16001) was dis-solved in 7.5 wt % DMSO.

TABLE 24

| | |
|---|---|
| enzyme peroxidase, solid: | 0-10 mg/g resin |
| DMSO: | 7.5 wt % |
| mediator (6-hydroxy-2-naphtoic acid): | 0.05 mmol/g resin |
| peroxide (Butanox M-50): | 0.5 wt % |

TABLE 25

| | | Results | | |
|---|---|---|---|---|
| enzyme, solid [mg/g resin] | gel-time [min] | Shore A after 2 h | Shore A after 24 h | Shore A after 48 h |
| 0.0 | n/a | x | x | x |
| 2.5 | 271 | x | 71 | 87 |
| 5.0 | 30 | 59 | 91 | 92 |
| 7.5 | 16 | 67 | 94 | 95 |
| 10.0 | 10 | 77 | 97 | 96 | x: no curing was detectable

The samples were prepared as described above (see sample preparation) using the amounts as described in table 26. Enzyme (peroxidase, Faizyme, #16001) was dissolved in 7.5 wt % DMSO.

TABLE 26

| | |
|---|---|
| enzyme peroxidase, solid: | 0-10 mg/g resin |
| DMSO: | 7.5 wt % |
| mediator (6-hydroxy-2-naphtoic acid): | 0.1 mmol/g resin |
| peroxide (Butanox M-50): | 0.5 wt % |

TABLE 27

| | | Results | | |
|---|---|---|---|---|
| enzyme, solid [mg/g resin] | geltime [min] | Shore A after 2 h | Shore A after 24 h | Shore A after 48 h |
| 0.00 | x | x | x | x |
| 0.25 | 1387 | x | x | 0* |
| 0.50 | 214 | 0 | 84 | 87 |
| 1.00 | 49 | 21 | 80 | 83 |
| 2.50 | 11 | 75 | 95 | 94 |
| 5.00 | 5 | 92 | 96 | 96 |
| 7.50 | 4 | 92 | 97 | 96 |
| 10.00 | 3 | 92 | 96 | 96 |

0*: Curing of sample was visible, but sample was too soft for measurement of Shore A hardness.

Also with DMSO, an increasing enzyme concentration lead to a decrease in gel-time and an increase in hardness.

Curing with $H_2O_2$ as Peroxide

The samples were prepared as described above (see sample preparation) using the amounts as described in table 28. The mediator 6-hydroxy-2-naphtoic acid and the enzyme (peroxidase, Faizyme, #16001) were dissolved in 10 wt % DMSO.

TABLE 28

| | |
|---|---|
| enzyme peroxidase, solid: | 10 mg/g resin |
| water/DMSO: | 10 wt % |
| mediator (6-hydroxy-2-naphtoesäure/ACAC): | 0.05 mmol/g resin |
| peroxide ($H_2O_2$, 30%): | 0.1-0.3 wt % |

TABLE 29

| | | Results | | |
|---|---|---|---|---|
| $H_2O_2$ (30%) [wt %] | gel-time [min] | Shore A after 2 h | Shore A after 24 h | Shore A after 48 h |
| 0.1 | n/a | x | 52 | 88 |
| 0.3 | n/a | x | 0* | 68 |

0*: Curing of sample was visible, but sample was too soft for measurement of Shore A hardness.
x: no curing was detectable In the following, the enzyme was dissolved in 10 wt % water and ACAC was used as mediator.

TABLE 30

| $H_2O_2$ (30%) [wt %] | gel-time [min] | Shore A after 2 h | Shore A after 24 h | Shore A after 48 h |
|---|---|---|---|---|
| 0.6 | n/a | x | 33 | 79 |

With both solvents (DMSO or water), curing of the resin with peroxidase and $H_2O_2$ was possible.

Curing of Thin Layers

The samples were prepared as described above (see sample preparation) using the amounts as described in table 30. The enzyme (peroxidase, Faizyme, #16001) was dissolved in 7.5 wt % DMSO.

TABLE 31

| | |
|---|---|
| enzyme peroxidase, solid: | 17 mg/g resin |
| mediator (6-hydroxy-2-naphtoic acid): | 0.05 mmol/g resin |
| peroxide (Butanox M-50) | 0.5 wt % |

The mixture was transferred to a glass plate and spread with a doctor blade (300 µm). The curing was tested via scratching the resin with a spatula. Additionally, a non-inventive comparison example with cobalt instead of the enzyme and mediator was tested.

Comparable curing with peroxidase or cobalt was observed. As a result, also thin film curing was possible with peroxidase.

Curing with Catalases

To test if the enzyme catalase can also be suitably used in the curing resin systems, the following experiment was carried out with catalase instead of peroxidase. The enzyme was dissolved in 10 wt % water.

TABLE 32

| | |
|---|---|
| enzyme catalase, solid: | 17 mg/g resin |
| water: | 10 wt % |
| mediator (ACAC): | 0.5 mmol/g resin |
| peroxide (Butanox M-50): | 0.5 wt % |

TABLE 33

| | | | Results | | |
|---|---|---|---|---|---|
| origin | supplier | article number | gel-time [min] | Shore A after 24 h | Shore A after 48 h |
| Bovine liver | Sigma | C40 | >120 | 0* | 0* |

0*: Curing of sample was visible, but sample was too soft for measurement of Shore A hardness.

Enzyme was dissolved in 10 wt % in a mixture of DMSO and water (50:50).

17

TABLE 34

| enzyme catalase, solid: | 17 mg/g resin |
| Dmso/water (50:50): | 10 wt % |
| peroxide (Butanox M-50): | 0.5 wt % |

TABLE 35

| | | | | Results | | |
| --- | --- | --- | --- | --- | --- | --- |
| origin | supplier | order no | geltime [min] | Shore A after 2 h | Shore A after 24 h | Shore A after 48 h |
| bovine liver | Sigma | C40 | n/a | x | x | 0* |
| bovine liver | Sigma Aldrich | E3289 | n/a | 0* | 16 | 37 |

0*: Curing of sample was visible, but sample was too soft for measurement of Shore A hardness.

The tables show that the employment of catalase also leads to the curing of the resin.

The invention claimed is:

1. A composition comprising
   a) a curable resin or prepolymer component having ethylenically unsaturated polymerizable groups,
   b) an ethylenically unsaturated polymerizable monomer,
   c) an oxidoreductase and
   d) at least one of an organic peroxide and hydrogen peroxide
   wherein the composition comprises 0.0 to 20.0% by weight of water, calculated on the total weight of the composition and all oxidoreductase in the composition act on peroxide as an electron receptor.

2. The composition according to claim 1, wherein the oxidoreductase is a peroxidase (EC 1.11.1).

3. The composition according to claim 2, wherein the peroxidase (EC 1.11.1) is one of a peroxidase (EC 1.11.1.7), catalase (EC 1.11.1.6) or mixtures thereof.

4. The composition according to claim 1, wherein the oxidoreductase is from plant, fungal, mammalian, yeast or bacterial origin.

5. The composition according to claim 1, wherein the amount of the oxidoreductase is in the range of 0.01 to 40.00 mg/g, based on the weight of components a)+b).

6. The composition according to claim 1, wherein the composition further comprises a mediator.

7. The composition according to claim 6, wherein the mediator is at least one of 6-hydroxy-2-naphtoic acid or Acetylacetone (ACAC).

8. The composition according to claim 1, wherein the composition is liquid at a temperature of 23° C.

9. The composition according to claim 1, wherein the composition comprises 0.0 to 40.0% of organic solvent.

10. The composition according to claim 1, wherein the composition further comprises dimethyl sulfoxide.

11. The composition according to claim 1, wherein the composition further comprises solid particles selected from fillers, pigments, fibers, and combinations thereof.

12. A kit of parts for preparing the composition according to claim 1, comprising
    I. a binder module comprising
       a) the curable resin or prepolymer component having ethylenically unsaturated polymerizable groups,
       b) the ethylenically unsaturated polymerizable monomer, and
       c) the oxidoreductase, and
    II. a hardener module comprising at least one of an organic peroxide and hydrogen peroxide,
    wherein each module comprises 0.0 to 20.0% by weight of water, calculated on the weight of the module.

13. A kit of parts for preparing the composition according to claim 1, comprising
    I. a binder module comprising
       a) the curable resin or prepolymer component having ethylenically unsaturated polymerizable groups,
       b) the ethylenically unsaturated polymerizable monomer,
    II. a hardener module comprising at least one of an organic peroxide and hydrogen peroxide, and
    III. an activator module comprising the oxidoreductase,
    wherein the binder module and the hardener module comprise 0.0 to 20.0% by weight of water, calculated on the weight of the module.

14. A process of forming a three-dimensional shaped part comprising the steps of
    i. providing a composition according to claim 1,
    ii. impregnating fibers with said composition and bringing the composition in a desired three-dimensional shape, and
    iii. curing the composition by radical polymerization.

15. The process according to claim 14, wherein step ii) is carried out by introducing said composition in a mold.

16. The process according to claim 14, further comprising the step of preparing said composition.

\* \* \* \* \*